United States Patent [19]

Yamamoto et al.

[11] Patent Number: 4,738,951

[45] Date of Patent: Apr. 19, 1988

[54] PERFUME COMPOSITION

[75] Inventors: Takeshi Yamamoto; Kazutoshi Sakurai; Susumu Watanabe; Atsushi Kinosaki, all of Tokyo, Japan

[73] Assignee: Takasago Perfumery Co., Ltd., Tokyo, Japan

[21] Appl. No.: 66,297

[22] Filed: Jun. 25, 1987

[30] Foreign Application Priority Data

Jun. 25, 1986 [JP] Japan ................................ 61-146993

[51] Int. Cl.$^4$ ................................................ A61K 7/46
[52] U.S. Cl. ...................................................... 512/20
[58] Field of Search ............................ 560/35; 512/20

[56] References Cited

U.S. PATENT DOCUMENTS 2,976,217 3/1961 Kreps .

OTHER PUBLICATIONS

Gupta et al., Indian J. Chem. Sect. B, vol. 22B(9), pp. 948-951 (1983).
Arctander et al., Perfume & Flavor Chemicals, Monogram, #1735 (1969).

*Primary Examiner*—James H. Reamer
*Attorney, Agent, or Firm*—Sughrue, Mion, Zinn, Macpeak, and Seas

[57] ABSTRACT

A perfume composition is disclosed, containing methyl l-3,7-dimethyl-7-hydroxyoctylideneanthranilate of the following formula (I):

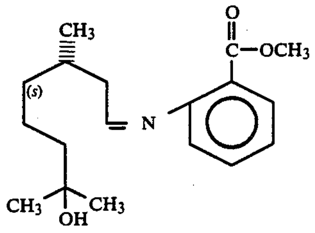

(I)

The perfume composition of the invention is less allergenic and safer than those containing the corresponding d- or dl-form. Further, the perfume composition has a less irritating odor and imparts a clean and green note.

3 Claims, 1 Drawing Sheet

PERFUME COMPOSITION

FIELD OF THE INVENTION

The present invention relates to a perfume composition and, in particular, to a perfume composition having a low sensitizing potential on skin.

BACKGROUND OF THE INVENTION

Methyl 3,7-dimethyl-7-hydroxyoctylideneanthranilate is a Schiff base compound, prepared from hydroxycitronellal (3,7-dimethyl-7-hydroxyoctanal) and methyl anthranilate. Hydroxycitronellal used as a starting material for the production of this compound is also a synthetic perfume and has chiefly been available in the form of either d-hydroxycitronellal that is obtained by hydrolysis of a sulfurous acid adduct of d-citronellal derived from citronella oil, or dl-hydroxycitronellal that is prepared from dl-citronellal which is prepared from myrcene. In other words, an l-form of hydroxycitronellal has seldom been used (see O. Okuda, *Koryo Kagaku Soran* (Review of Perfume Chemistry), p. 753, Hirokawa Publishing Company, 1968).

Therefore, methyl 3,7-dimethyl-7-hydroxyoctylideneanthranilate has generally been known only in its d- or dl-form. Being a classical fragrance raw material having an orange flower note, methyl 3,7-dimethyl-7-hydroxyoctylideneanthranilate has been recognized as an indispensable aroma chemical that is compounded for manufacturing perfumes within the class of floral family (see Steffen and Arctander, *Perfume and Flavor Chemicals Monograph,* No. 1735 (1969)). However, no case has been reported of success in isolating the l-form of methyl 3,7-dimethyl-7-hydroxyoctylideneanthranilate or in identifying its fragrance and properties. There has also been no report on the characteristics or safety features of this compound as a perfume.

With the recent concern over the safety of perfumes, there is a global need to create perfumes that present much less hazard to human health. In this connection, it has been reported that hydroxycitronellal which is not only a synthetic perfume per se but also used as a starting material for the production of methyl 3,7-dimethyl-7-hydroxyoctylideneanthranilate has a potential for causing dermatitis when it is used in a cream base (see H. Nakayama, *Perfume Allergy and Patch Test* in Perfume Chemistry Books, No. 1, Fragrance Journal Publishing Company, p. 78 (1983)). This suggests the possibility that the conventionally used methyl 3,7-dimethyl-7-hydroxyoctylideneanthranilate also has a potential for causing contact allergy. If so, this compound cannot be used in the preparation of perfumes of either the citrus or neroli family. Therefore, development of a substitute that has the closest resemblance to the conventional methyl 3,7-dimethyl-7-hydroxyoctylideneanthranilate not only in terms of fragrance but also with respect to other properties such as solubility is strongly desired.

The present inventors synthesized various aldehyde compounds, reacted them with methyl anthranilate to prepare Schiff bases, and investigated the safety and other characteristics of these Schiff bases used as perfumes. During the course of these studies, the present inventors established a method of synthesizing l-hydroxycitronellal (see Japanese Patent Application (OPI) No. 4748/1983) with the attendant finding that the l-form of hydroxycitronellal has a very low level of allergenicity as compared with its d-form. (The term "OPI" as used herein refers to a "published unexamined Japanese patent application".)

In addition to the note of fragrance and solubility of the Schiff bases, the present inventors investigated their potential to cause contact allergy (or sensitization) by conducting an allergenicity test on guinea pigs with a view to searching for a substitute that is safer to use and which yet provides a note of fragrance that is not much different from those of the conventional isomers of hydroxycitronellal. As a result, the present inventors found that only methyl 3,7-dimethyl-7-hydroxyoctylideneanthranilate is acceptable because of its balanced properties, i.e., very low sensitizing potential, note for fragrance that is not much different from those of other isomeric forms of hydroxycitronellal, less irritating odor, cleanness, and an added green note. The present invention has been accomplished on the basis of this finding.

SUMMARY OF THE INVENTION

An object of the present invention is to provide a perfume composition containing methyl l-3,7-dimethyl-7-hydroxyoctylideneanthranilate of the following formula (I):

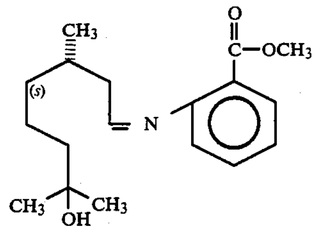

(I)

DETAILED DESCRIPTION OF THE INVENTION

Figure 1:
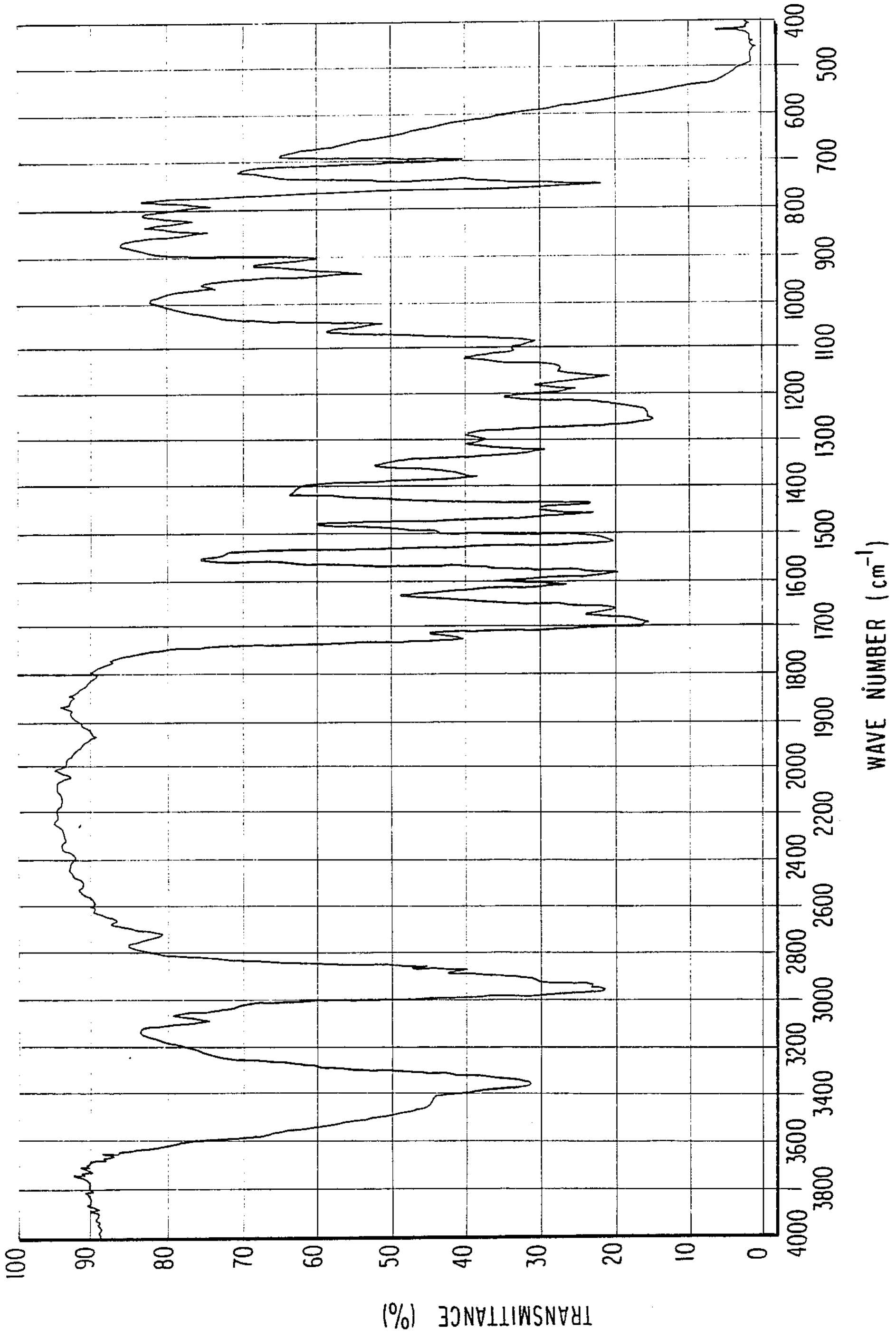
FIG. 1 is an infrared spectrum of methyl l-3,7-dimethyl-7-hydroxyoctylideneanthranilate produced in Preparation Example 1.

Methyl l-3,7-dimethyl-7-hydroxyoctylideneanthranilate represented by formula (I) can be prepared by one of the following two routes:

(1) (−)-8-Hydroxy-$\Delta^4$-menthen-3-one derived from (+)-pulegone is reacted with alkaline hydrogen peroxide to obtain (+)-8-hydroxy-4,5α-epoxyisomenthone which is then reacted with tosyl hydrazine to form (−)-7-hydroxy-3,7-dimethylocto-5-in-1-al which is subsequently hydrogenated (see *Helv. Chimica Acta.,* 54, 1797 (1971)); and (2) According to the method described in Example 3 in the specification of Japanese Patent Application (OPI) No. 4748/1983 or the method described in *J. Am. Chem. Soc.,* 106, 5208 (1984), N,N-diethyl-7-hydroxygeranylamine ((E)-N,N-diethyl-7-hydroxy-3,7-dimethyl-2-octenylamine) or N,N-diethyl-7-hydroxycinerylamine ((Z)-N,N-diethyl-7-hydroxy-3,7-dimethyl-2-octenylamine) is asymmetrically isomerized with $[Rh((+)\text{-BINAP})(NBD)]^+ClO_4^-$ or $[Rh((-)\text{-BINAP})(NBD)]^+ClO_4^-$ to form an enamine of (−)-7-hydroxycitronellal which is then hydrolyzed, wherein NBD means norbornadiene, and BINAP means 2,2′-bis(diphenylphosphono)-1,1′-binaphthyl.

By employing either one of these methods, (−)-7-hydroxycitronellal having a boiling point of from 85° to 90° C./2 mmHg and a specific rotation $[\alpha]_D^{23}$ of −12° (C=20, benzene) is obtained. When this substance is reacted with methyl anthranilate by a known method, the intended methyl l-3,7-dimethyl-7-hydroxyoctylideneanthranilate of formula (I) is formed. This substance is a yellow viscous liquid having an orange-flower note.

The contact allergenic (or sensitizing) potential of this substance was compared with those of the conventional d- and dl-forms of methyl 3,7-dimethyl-7-hydroxyoctylideneanthranilate by conducting the following maximization test according to the method described in B. Magnusson and A. M. Kligman, *J. Inv. Derm.*, 52, 268–276 (1976).

The results were evaluated after the lapse of a predetermined period. The sensitized potential of guinea pigs that were challenged with the l-form after induction with the l-form was weaker than that of those that were challenged with the d- and dl-forms after induction with the d- and dl-forms, respectively. The same results were observed such that the sensitized potential of guinea pigs that were challenged with the d-, dl-, or l-form after induction with the dl-form was weaker than that of those that were challenged with d-, l-, and dl-forms after induction with the d- or dl-form. In addition, the sensitized potential of guinea pigs that were challenged with the l-form after induction with the d- or dl-form was also of a weaker level in the cross-section. For these reasons, the use of the l-form of methyl 3,7-dimethyl-7-hydroxyoctylideneanthranilate is recommended.

When this compound, i.e., methyl l-3,7-dimethyl-7-hydroxyoctylideneanthranilate, is used in a perfume composition, it can find extensive utility in the manufacture of compounded perfumes in the citrus or neroli family that have a fragrance of the same orange-flower note as imparted by the heretofore used isomers. This compound may be used in an amount of from 0.1 to 50 wt%, preferably from 0.5 to 20 wt%, of the perfume composition. In addition to this active compound, the perfume composition of the present invention may contain commonly employed additives for perfumes in appropriate amounts. The perfume composition may be formulated in any desired dosage form.

The following examples and test example are provided for the purpose of further illustrating the present invention but are in no sense to be taken as limiting.

PREPARATION EXAMPLE 1

172 g (1 mole) of l-hydroxycitronellal (prepared in accordance with Example 3 of Japanese Patent Application (OPI) No. 4748/1983) and 151 g (1 mole) of methyl anthranilate were charged into a 500-ml distillation flask and heated at 80° C. at a reduced pressure of 10 mmHg over about 15 hours so as to remove the reaction water formed in a stoichiometric amount (17.9 g).

As a result of this reaction, methyl l-3,7-dimethyl-7-hydroxyoctylideneanthranilate was obtained as a yellow viscous liquid having a specific gravity $d_{20}^{20}$ of 1.0575, a refractive index $n_D^{20}$ of 1.5312, and a specific rotation $[\alpha]_D^{20}$ of −6.73°. The IR spectrum of this substance is shown in FIG. 1. The fragrance of this substance had an orange-flower note similar to that of the conventional d- or dl-form of methyl 3,7-dimethyl-7-hydroxyoctylideneanthranilate. However, this substance had a less irritating odor and had a clean and slightly green note; therefore, the impression of this substance was that it was of higher quality than the other forms.

TEST EXAMPLE

Delayed contact hypersensitivity test in guinea pigs: (Guinea pig maximization test)

1. Animal:

Albino guinea pigs of the Hartley/Dunkin strain 350–400 g body weight, female

Test sample: 10 animals

Negative control: 10 animals

Positive control: 3 animals

2. Sample:

Induction and topical application:

Test sample: 10% Perfume in Freund's complete adjuvant (FCA)

Positive control: 10% cinnamic aldehyde in FCA

Challenge:

Open method

Vehicle: acetone

Concentration: 20% and 10% in acetone

3. Method:

(a) Induction:

The induction procedure consists of two-stage operation.

(i) Intra-dermal injections: Two row of three injections are placed within an area 2×4 cm in the shoulder region.

The three injections are, Freund's adjuvant alone (50%, 0.1 ml), test agent alone (10% in FCA, 0.1 ml), and test agent emulsified in the adjuvant (10% in the adjuvant emulsified with water, 0.1 ml)

(ii) Topical application: One week after injections to enhance the sensitization, the same area clipped and shaved is pretreated with 10% sodium lauryl sulfate (SLS) in petrolatum 24 hours before the application of the test material to provoke mild inflammatory reaction.

The SLS is massaged into the skin with a glass rod. No bandage is applied. 0.2 ml of 10% test material in FCA is spread over a 2×4 cm patch of Toyo filter paper. The patch is overed by an overlapping strip of 1½" 3M Blenderm plastic tape.

This in turn is firmly secured for 48 hours by elastic adhesive Steri Drap, 4 cm in width, wound around the torso of the animal.

For control group, water instead of the test material is used.

(b) Challenge procedure:

Challenge is by topical application. The animals are challenged three weeks after the intradermal injections. The hair of the flank is removed by clipping and shaving.

Challenge test is performed by applying with a pipette 0.02 ml of 10% or 20% of the test material to the left and right flank skin areas (1.5 cm×1.5 cm/each site). The application sites are left uncovered. Positive and negative controls are done samely.

4. Reading of challenge reactions:

The challenge sites are evaluated after 24 and 48 hours according to the criteria of Draze produced in the following table.

Criteria for assessment of sensitization:

| | Score |
|---|---|
| (i) Erythema Formation | |
| No erythema | 0 |

-continued

| | Score |
|---|---|
| Very slight erythema (barely perceptible) | 1 |
| Well-defined erythema | 2 |
| Moderate to severe erythema | 3 |
| Severe erythema (best redness) to slight eschar formation (injury in depth) | 4 |
| (ii) Edema Formation | |
| No edema | 0 |
| Slight edema (edges of area well defined by definite raising) | 1 |
| Moderate edema (raised approx. 1 mm) | 2 |
| Severe edema (raised more than 1 mm and extending beyond the area of exposure) | 3 |

$$\underset{(P.R.)}{\text{Positive response}} = \frac{\text{number of positive animals}}{\text{number of tested animals}}$$

$$\underset{(M.R.)}{\text{Mean response}} = \frac{\Sigma[(i) + (ii)]}{\text{number of tested animals}}$$

5. Judgement:

The skin reaction is positive:

The value of P.R. is higher than 0.6 or that of M.R. is higher than 1.0.

TABLE 1

| Inducer (concentration: 10%) | Challenge substance and its concentration (%) | Sensitized group 24 hrs. ($A_1$) I | II | 48 hrs. ($A_2$) I | II | 72 hrs. ($A_3$) I | II | Control group 24 hrs. ($a_1$) I | II | 48 hrs. ($a_2$) I | II | 72 hrs. ($a_3$) I | II | Judgement $A_1$-$a_1$ | | $A_2$-$a_2$ | | $A_3$-$a_3$ | |
|---|---|---|---|---|---|---|---|---|---|---|---|---|---|---|---|---|---|---|---|
| d-form | d-form (20) | 10/10 | 3.1 | 10/10 | 3.0 | 10/10 | 2.4 | 0/10 | 0 | 0/10 | 0 | 0/10 | 0 | 10/10 | 3.1 | 10/10 | 3.0 | 10/10 | 2.4 |
| d-form | d-form (10) | 10/10 | 2.2 | 10/10 | 2.2 | 10/10 | 1.8 | 0/10 | 0 | 0/10 | 0 | 0/10 | 0 | 10/10 | 2.2 | 10/10 | 2.2 | 10/10 | 1.8 |
| d-form | l-form (20) | 5/10 | 0.5 | 4/10 | 0.4 | 3/10 | 0.3 | 0/10 | 0 | 0/10 | 0 | 0/10 | 0 | 5/10 | 0.5 | 4/10 | 0.4 | 3/10 | 0.3 |
| dl-form | d-form (10) | 10/10 | 2.6 | 10/10 | 2.6 | 10/10 | 2.5 | 0/10 | 0 | 0/10 | 0 | 0/10 | 0 | 10/10 | 2.6 | 10/10 | 2.6 | 10/10 | 2.5 |
| dl-form | dl-form (10) | 10/10 | 2.2 | 10/10 | 2.0 | 10/10 | 1.9 | 0/10 | 0 | 0/10 | 0 | 0/10 | 0 | 10/10 | 2.2 | 10/10 | 2.0 | 10/10 | 1.9 |
| dl-form | l-form (10) | 10/10 | 1.7 | 10/10 | 1.4 | 10/10 | 1.2 | 0/10 | 0 | 0/10 | 0 | 0/10 | 0 | 10/10 | 1.7 | 10/10 | 1.4 | 10/10 | 1.2 |
| l-form | l-form (20) | 7/10 | 1.6 | 7/10 | 1.6 | 7/10 | 1.4 | 0/10 | 0 | 0/10 | 0 | 0/10 | 0 | 7/10 | 1.6 | 7/10 | 1.6 | 7/10 | 1.4 |
| l-form | l-form (10) | 6/10 | 1.1 | 6/10 | 1.2 | 5/10 | 0.9 | 0/10 | 0 | 0/10 | 0 | 0/10 | 0 | 6/10 | 1.1 | 6/10 | 1.2 | 5/10 | 0.9 |
| l-form | d-form (20) | 6/10 | 1.3 | 7/10 | 1.5 | 6/10 | 1.2 | 0/10 | 0 | 0/10 | 0 | 0/10 | 0 | 6/10 | 1.3 | 7/10 | 1.5 | 6/10 | 1.2 |

I: positivity;
II: score point

As is clear from Table 1, the guinea pigs that had been challenged with the d-form (concentration: 20%) after induction with the d-form had a score of 3.0 at the 48th-hour evaluation, whereas those challenged with the l-form (20%) had a score of only 0.4, and the difference was significant. However, the animals that had been challenged with the d-form (20%) and the l-form (20%) after induction with the l-form had substantially equal scores (1.5 to 1.6, respectively), with no significant difference, at the 48th-hour evaluation. These values (1.5 to 1.6) were about one half of the score of the animals that had been challenged with the d-form (20%) after induction with the d-form. Similar results were observed at both evaluations conducted after 24 and 72 hours.

The animals that had been sensitized by induction with the dl-form exhibited the highest score when they were challenged with the d-form and displayed the lowest score when challenged with the l-form; these results were consistently attained irrespective of the time of evaluation.

The above data suggests the low potential of the l-form of methyl 3,7-dimethyl-7-hydroxyoctylideneanthranilate to cause contact sensitization, and this is so even if induction has already been performed with the d- or dl-form.

EXAMPLE 1

Using the methyl l-3,7-dimethyl-7-hydroxyoctylideneanthranilate made in Preparation Example 1, an orange-flower compounded perfume having a floral odor was prepared in accordance with the formulation indicated below.

| Components | Parts by weight |
|---|---|
| linalool | 35 |
| methyl naphthyl ketone | 15 |
| methyl l-3,7-dimethyl-7-hydroxyoctylideneanthranilate | 18 |
| phenylethyl alcohol | 14 |
| neroli oil | 1.5 |
| petigrain citronia | 4 |
| bergamot | 2 |
| linalyl acetate | 8 |
| dl-hydroxycitronellal | 4 |
| orange flower absolute | 1 |
| indole (10%) | 1 |
| geranyl acetate | 2 |
| petigrain Paraguay | 0.5 |

The resulting compounded perfume was much milder, had a stronger green note, and presented a fresher floral odor than the perfumes incorporating the corresponding d- or dl-form. In addition, this compounded perfume had no irritating odor.

EXAMPLE 2

Using the methyl l-3,7-dimethyl-7-hydroxyoctylideneanthranilate made in Preparation Example 1, a tuberose compounded perfume was prepared in accordance with the formulation indicated below.

| Components | Parts by weight |
|---|---|
| γ-nonyl lactone | 10.0 |
| celery-seed oil | 1.5 |
| α-n-amylcinnamic aldehyde | 7.5 |
| benzyl acetate | 6.0 |
| methyl benzoate | 10.0 |
| labdanum clair | 2.0 |
| tuberose absolute | 5.0 |
| methyl salicylate | 3.5 |
| ylang ylang oil | 12.5 |
| piperonal | 3.0 |
| methyl l-3,7-dimethyl-7-hydroxyoctylideneanthranilate | 35.0 |
| balsam pure | 5.0 |
| geranyl formate | 2.0 |
| p-cresyl phenylacetate | 2.0 |
| benzyl benzoate | 5.0 |

The resulting compounded perfume was much milder and had a stronger green note than the perfumes incorporating d- or dl-form. In addition, this compounded perfume had no irritating odor.

The perfume composition of the present invention employs methyl l-3,7-dimethyl-7-hydroxyoctylideneanthranilate as an aroma chemical and is less allergenic and, hence, safer than perfumes incorporating the corresponding d- or dl-form. As a further advantage, a perfume that has a less irritating odor, is clean and which imparts a mild green note can be compounded using this l-form of methyl 3,7-dimethyl-7-hydroxyoctylideneanthranilate. Such a perfume can surely gain commercial acceptance.

While the invention has been described in detail and with reference to specific embodiments thereof, it will be apparent to one skilled in the art that various changes and modifications can be made therein without departing from the spirit and scope thereof.

What is claimed is:

1. A perfume composition containing methyl l-3,7-dimethyl-7-hydroxyoctylideneanthranilate of the following formula (I):

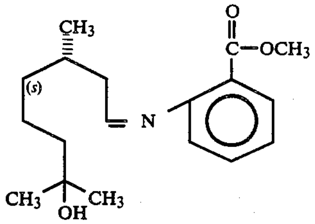

(I)

2. A perfume composition as in claim 1, wherein said methyl l-3,7-dimethyl-7-hydroxyoctylideneanthranilate is contained in an amount of from 0.1 to 50 wt% of the composition.

3. A perfume composition as in claim 2, wherein said methyl l-3,7-dimethyl-7-hydroxyoctylideneanthranilate is contained in an amount of from 0.5 to 20 wt% of the composition.

* * * * *